(12) United States Patent
Gschwind et al.

(10) Patent No.: US 9,717,673 B2
(45) Date of Patent: Aug. 1, 2017

(54) SHAMPOO PREPARATIONS

(71) Applicant: DSM IP ASSETS B.V., Heerlen (NL)

(72) Inventors: Svenja Gschwind, Basel (CH); Dirk Weber, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 79 days.

(21) Appl. No.: 14/389,878

(22) PCT Filed: Mar. 25, 2013

(86) PCT No.: PCT/EP2013/056260
§ 371 (c)(1),
(2) Date: Oct. 1, 2014

(87) PCT Pub. No.: WO2013/149873
PCT Pub. Date: Oct. 10, 2013

(65) Prior Publication Data
US 2015/0328126 A1    Nov. 19, 2015

(30) Foreign Application Priority Data

Apr. 2, 2012 (EP) ..................... 12162881

(51) Int. Cl.
| | |
|---|---|
| A61K 8/72 | (2006.01) |
| A61K 8/81 | (2006.01) |
| A61K 8/46 | (2006.01) |
| A61K 8/42 | (2006.01) |
| A61Q 5/02 | (2006.01) |
| A61Q 5/06 | (2006.01) |

(52) U.S. Cl.
CPC .............. *A61K 8/8152* (2013.01); *A61K 8/42* (2013.01); *A61K 8/463* (2013.01); *A61Q 5/02* (2013.01); *A61Q 5/06* (2013.01); *A61K 2800/596* (2013.01)

(58) Field of Classification Search
None
See application file for complete search history.

(56) References Cited

U.S. PATENT DOCUMENTS

| | | | |
|---|---|---|---|
| 5,413,775 A | * 5/1995 | Hatfield | ................. A61K 8/046 424/47 |
| 2002/0119113 A1 | * 8/2002 | Ellis | ........................ A61K 8/14 424/70.22 |

FOREIGN PATENT DOCUMENTS

| | | | | |
|---|---|---|---|---|
| DE | 43 14 305 | | 11/1994 | |
| EP | 0 805 169 | | 11/1997 | |
| WO | WO 2011/057882 | * | 5/2011 | ............ C08F 220/18 |
| WO | WO 2011/058163 | | 5/2011 | |
| WO | WO 2012/072774 | | 6/2012 | |

OTHER PUBLICATIONS

International Search Report for PCT/EP2013/056260, mailed Feb. 17, 2014.

* cited by examiner

*Primary Examiner* — Jake Vu

(74) *Attorney, Agent, or Firm* — Nixon & Vanderhye P.C.

(57) ABSTRACT

The invention relates to shampoo preparations comprising water, an acrylic emulsion polymer and at least one surfactant. The preparations provide improved styling performance and improved hair feel.

9 Claims, No Drawings

SHAMPOO PREPARATIONS

This application is the U.S. national phase of International Application No. PCT/EP2013/056260 filed 25 Mar. 2013 which designated the U.S. and claims priority to EP Patent Application No. 12162881.2 filed 2 Apr. 2012, the entire contents of each of which are hereby incorporated by reference.

The invention relates to shampoo preparations comprising water, an acrylic emulsion polymer and at least one surfactant. The preparations provide improved styling performance and improved hair feel.

Many hair shampoo preparations provide acceptable cleaning but provide little or no styling benefits, e.g. body, hold, stiffness. To realize such benefits, separate cleaning and styling products are often used.

Thus, there is an ongoing need for shampoo preparations which provide next to a good cleaning performance also good styling attributes to the hair without making the hair dull, sticky and stiff but leave the dry hair both feeling and looking natural and soft. Furthermore, the shampoo preparation should preferably exhibit good foaming properties.

Surprisingly it has been found, that shampoo preparations comprising water, a specific acrylic emulsion polymer and at least one surfactant provide good styling attributes to the hair without resulting in an unacceptable hair feel. It has furthermore been found that good foaming properties can be achieved, if the acrylic emulsion polymer is neutralized to a degree of at least 50%.

Thus, in one embodiment the invention relates to a shampoo preparation comprising water, at least one surfactant and an effective amount of an acrylic emulsion polymer obtained by emulsion polymerization of a monomer composition consisting of a mixture of methacrylic acid, ethyl acrylate and n-butyl methacrylate.

The term shampoo preparations relates to any liquid or cream preparations of soap or detergent used to wash the hair and scalp.

The term 'consisting of' as used according to the present invention means that the total amount of monomer ideally sum up to 100 wt.-%. It is however not excluded that small amount of impurities or additives may be present such as e.g. in amounts of less than 5 wt.-%, preferably less than 3 wt.-% which are e.g. introduced via the respective raw materials.

The term "effective amount" means an amount that can achieve the stated results. In particular, the term "effective amount" refers to a concentration (based on solids) of at least 0.01 wt.-% based on the total weight of the shampoo preparation. Preferably, a concentration of 0.01-20 wt.-%, most preferred of 0.1-15 wt.-%, in particular in the range of 1 to 10 wt.-% such most in particular in the range of 1 to 7 wt.-% of the acrylic emulsion polymer is used.

In all embodiments of the invention the monomer composition preferably consists of a mixture of 10-30 wt.-% of methacrylic acid, 5-15 wt.-% of ethyl acrylate and 60-80 wt.-% of n-butyl methacrylate, more preferably of a mixture of 10-30 wt.-% of methacrylic acid, 5-15 wt.-% of ethyl acrylate and 60-80 wt.-% of n-butyl methacrylate, most preferably of a mixture of 15-25 wt.-% of methacrylic acid, 8-12 wt.-% of ethyl acrylate and 65-75 wt.-% of n-butyl methacrylate, such as even more in particular of 18-23 wt.-% of methacrylic acid, 9-11 wt.-% of ethyl acrylate and 67-72 wt.-% of n-butyl methacrylate.

The total amount of surfactant(s) (including any co-surfactant(s), and/or emulsifier(s)) in the shampoo preparation according to the present invention is preferably selected in the range of 0.1-40 wt.-%, such as more preferably in the range of 1-25 wt.-%, such as most preferably in the range of 5 to 20 wt.-%, based on the total weight of the shampoo preparation.

Preferably at least one anionic surfactant is present in the shampoo preparation according to the present invention.

Examples of suitable anionic surfactants are the alkyl sulfates, alkyl ether sulfates, alkylaryl sulphonates, alkanoyl isothionates, alkyl succinates, alkyl sulphosuccinates, alkyl ether sulphosuccinates, N-alkyl sarcosinates, alkyl phosphates, alkyl ether phosphates, and alkyl ether carboxylic acids and salts thereof, especially their sodium, magnesium, ammonium or mono-, di- or triethanolamine salts. The alkyl and acyl groups generally contain from 8 to 18, preferably from 10 to 16, carbon atoms and may be unsaturated. The alkyl ether sulfates, alkyl ether sulphosuccinates, alkyl ether phosphates and alkyl ether carboxylic acids and salts thereof may contain from 1 to 20 ethylene oxide or propylene oxide units per molecule.

In particular, the anionic surfactants are selected from sodium oleyl succinate, ammonium lauryl sulphosuccinate, sodium lauryl sulfate, sodium lauryl ether sulfate (also known as sodium laureth sulfate, SLES), sodium lauryl ether sulphosuccinate, ammonium lauryl sulfate (ALS), ammonium lauryl ether sulfate (ammonium laureth sulfate), sodium dodecylbenzene sulphonate, triethanolamine dodecylbenzene sulphonate, sodium cocoyl isethionate, sodium lauryl isethionate, lauryl ether carboxylic acid and sodium N-lauryl sarcosinate or mixtures thereof. Preferred anionic surfactants are sodium lauryl sulfate, sodium lauryl ether sulfate (n) EO, (where n is from 1 to 4, in particular n is 3), sodium lauryl ether sulphosuccinate (n) EO, (where n is from 1 to 4, in particular n is 3), ammonium lauryl sulfate, ammonium lauryl ether sulfate (n) EO, (where n is from 1 to 4, in particular n is 3) or mixtures thereof.

In all embodiments of the present invention the anionic surfactant is preferably selected from sodium lauryl sulfate, ammonium lauryl sulfate, sodium lauryl ether sulfate, ammonium lauryl ether sulfate, sodium lauroyl sarconisate, sodium oleylsuccinate, ammonium lauryl sulfosuccinate, sodium dodecylbenzol sulfonate and/or triethanolamine dodecylbenzol sulfonate or mixtures thereof. Most preferably in all embodiments of the invention the anionic surfactant is selected from sodium lauryl sulfate, ammonium lauryl sulfate, sodium lauryl ether sulfate (also known as sodium Laureth sulfate) and/or ammonium lauryl ether sulfate. Particularly preferred in all embodiments of the invention is the use sodium lauryl ether sulfate e.g. available as Texapon® NSO-B at Caelo.

The total amount of the anionic surfactant(s) in the shampoo preparations according to the present invention is preferably selected in the range of 0.1 to 25 wt.-%, more preferably in the range of 5 to 20 wt.-%, most preferably in the range of 2 to 15 wt.-%, based on the total weight of the shampoo preparation.

In all embodiments of the invention the weight-ratio of the anionic surfactant to the acrylic emulsion polymer is preferably in the range of 5:1 to 0.3:1, in particular 3:1 to 0.5:1.

In a particular preferred embodiment the invention relates to a shampoo preparation wherein the anionic surfactant is selected from sodium lauryl sulfate, ammonium lauryl sulfate, sodium lauryl ether sulfate and/or ammonium lauryl ether sulfate and the ratio of the anionic surfactant to the acrylic emulsion polymer is selected in the range of about 5 to 1 to 0.3 to 1, such as in particular in the range of 3 to 1 to 0.5 to 1.

The acrylic emulsion polymers according to the invention are prepared by emulsion polymerization methods according to known methods as e.g. described in EP10193512.0.

The method of free-radically initiated aqueous emulsion polymerization has been described previously on many occasions and is therefore sufficiently known to the person skilled in the art [cf. e.g. Encyclopedia of Polymer Science and Engineering, Vol. 8, pages 659 to 677, John Wiley & Sons, Inc., 1987; D. C. Blackley, Emulsion Polymerization, pages 155 to 465, Applied Science Publishers, Ltd., Essex, 1975; D. C. Blackley, Polymer Latices, 2.sup.nd Edition, Vol. 1, pages 33 to 415, Chapman & Hall, 1997; H. Warson, The Applications of Synthetic Resin Emulsions, pages 49 to 244, Ernest Benn, Ltd., London, 1972; D. Diederich, Chemie in unserer Zeit [Chemistry of our Time] 1990, 24, pages 135 to 142, Verlag Chemie, Weinheim; J. Piirma, Emulsion Polymerization, pages 1 to 287, Academic Press, 1982; F. Holscher, Dispersionen synthetischer Hochpolymerer [Dispersions of Synthetic High Polymers], pages 1 to 160, Springer-Verlag, Berlin, 1969 and DE-A 40 03422]. The free-radically initiated aqueous emulsion polymerization is usually carried out by dispersely distributing the monomers, usually with co-use of dispersants, in the aqueous medium, and polymerizing using at least one free-radical polymerization initiator.

Suitable free-radical polymerization initiators for the free-radical aqueous emulsion polymerization according to the invention are all those which are able to trigger a free-radical aqueous emulsion polymerization. These may in principle be either peroxides or azo compounds. Redox initiator systems are of course also suitable. Peroxides which may be used are, in principle, inorganic peroxides, such as hydrogen peroxide or peroxodisulfates, such as the mono- or di-alkali metal or ammonium salts of peroxide disulfuric acid, for example, its mono- and di-sodium, -potassium or ammonium salts or organic peroxides, such as alkyl hydroperoxides, for example tert-butyl, p-menthyl or cumyl hydroperoxide, tert-butyl perpivalate, and dialkyl or diaryl peroxides, such as di-tert-butyl or di-cumyl peroxide, 2,5-dimethyl-2,5-di(t)butyl-peroxy(hexane) or dibenzoyl peroxide.

The azo compounds used are essentially 2,2'-azobis (isobutyronitrile), 2,2'-azobis(2,4-dimethylvaleronitrile) and 2,2'-azobis(amidinopropyl)dihydrochloride (AIBA, corresponds to V-50™ from Wako Chemicals), 1,1'-azobis(1-cyclohexanecarbonitrile), 2,2'-azobis(2-amidinopropane) salts, 4,4'-azobis(4-cyanovaleric acid) or 2-(carbamoylazo) isobutyronitrile.

Suitable oxidizing agents for redox initiator systems are essentially the abovementioned peroxides. Corresponding reducing agents which may be used are sulfur compounds with a low oxidation state, such as alkali metal sulfites, for example potassium and/or sodium sulfite, alkali metal hydrogensulfites, for example potassium and/or sodium hydrogen sulfite, alkali metal metabisulfites, for example potassium and/or sodium metabisulfite, formaldehyde sulfoxylates, for example potassium and/or sodium formaldehyde sulfoxylate, alkali metal salts, specifically potassium and/or sodium salts, of aliphatic sulfinic acids (i.e. Brugolite® FF6) and alkali metal hydrogen sulfides, such as, for example, potassium and/or sodium hydrogen sulfide, salts of polyvalent metals, such as iron(II) sulfate, iron(II) ammonium sulfate, iron(II) phosphate, enediols, such as dihydroxymaleic acid, benzoin and/or (i-) ascorbic acid, and reducing saccharides, such as sorbose, glucose, fructose and/or dihydroxyacetone.

The initiators are usually used in amounts up to 10% by weight, preferably 0.02 to 5% by weight, based on the monomers to be polymerized.

Surfactants can be utilized in order to assist the dispersion of the polymer in water. Suitable surfactants include but are not limited to conventional anionic and/or non-ionic surfactants and mixtures thereof such as Na, K and $NH_4$ salts of dialkylsulphosuccinates, Na, K and $NH_4$ salts of sulphated oils, Na, K and $NH_4$ salts of alkyl sulphonic acids, Na, K and $NH_4$ alkyl sulphates, alkali metal salts of sulphonic acids; fatty alcohols, ethoxylated fatty acids and/or fatty amides, and Na, K and $NH_4$ salts of fatty acids such as Na stearate and Na oleate. Other anionic surfactants include alkyl or (alk)aryl groups linked to sulphonic acid groups, sulphuric acid half ester groups (linked in turn to polyglycol ether groups), phosphonic acid groups, phosphoric acid analogues and phosphates or carboxylic acid groups. Non-ionic surfactants include polyglycol ether compounds and preferably polyethylene oxide compounds as disclosed in "Non-Ionic Surfactants—Physical Chemistry" edited by M. J. Schick, M. Decker 1987. The amount of surfactant used is preferably 0 to 15 wt.-% by, more preferably 0 to 8 wt-%, still more preferably 0 to 5% wt.-%, especially 0.1 to 3 wt-% and most especially 0.3 to 2 wt-% on the total weight of vinyl monomers required.

Chain transfer agent may be added to control the molecular weight. Suitable chain transfer agents include mercaptans such as n-dodecylmercaptan, n-octylmercaptan, t-dodecylmercaptan, mercaptoethanol, iso-octyl thioglycolate, $C_2$ to $C_8$ mercapto carboxylic acids and esters thereof such as 3-mercaptopropionic acid and 2-mercaptopropionic acid. Mixtures of two or more regulators may also be used.

Preferably 0.05 to 5 wt-%, more preferably 0.1 to 3 wt-% and most preferably 0.1 to 1 wt-% of chain transfer agent based on the weight of vinyl monomers required is used. The alkanethiols are usually added to the polymerization together with the monomers.

If, in the polymerization, thiols are used, a subsequent hydrogen peroxide treatment could be required in order to obtain polymers with a neutral odor.

The emulsion polymerization usually takes place with the exclusion of oxygen, for example under a nitrogen or argon atmosphere, at temperatures in the range from 20 to 200° C. Polymerization temperatures in the range from 50 to 130° C., in particular 70 to 95° C. are advantageous.

The polymerization can be carried out batch-wise, semi-continuously or continuously. The polymerization and the monomer and regulator feed are often carried out semi-continuously by the feed method. Preferably, at least some of the monomers, initiators and, if appropriate, regulators are metered into the reaction vessel uniformly throughout the polymerization. However, it is also possible to have an initial charge of the monomers and the initiator in the reactor and to polymerize them, with cooling if appropriate. Another option is to carry out the polymerization using seed latex prepared from the polymers to be polymerized in the first polymerization phase. The remainder of the monomer mixture is added, preferably by the feed method.

The polymerization reaction advantageously takes place until the monomer conversion is >95% by weight, preferably >98% by weight or >99% by weight.

It is often useful if the aqueous polymer dispersion obtained is subjected to an after-polymerization step in order to reduce further the amount of unreacted monomer. This measure is known to the person skilled in the art (for example EP-B 3957, EP-B 28348, EP-B 563726, EP-A 764699, EP-A 767180, DE-A 3718520, DE-A 3834734, DE-A4232194, DE-A 19529599, DE-A 19741187, DE-A 19839199, DE-A 19840586, WO 95/33775 or U.S. Pat. No. 4,529,753). It is of course also possible to subject the aqueous polymer dispersion obtained to an inert-gas and/or steam stripping, likewise known to the person skilled in the art, before or after the after-polymerization step. This stripping operation preferably takes place after the after-polymerization step. As is described in EP-A 805169, partial neutralization of the dispersion to a pH in the range from 5 to 7, preferably to a pH in the range from 5.5 to 6.5, is advantageous before the physical deodorization.

If applicable, due to a low monomer content after preparation, these possible additional steps can be omitted and the dispersions can be further used as such providing an economical advantage.

In a preferred embodiment, the aqueous polymer dispersion obtained is subjected to a post initiation (post treatment/after-polymerization) using t-butyl hydroperoxide with iso-ascorbic acid or t-butyl hydroperoxide with aliphatic sulfinic acids (i.e. Bruggolite® FF6) in water. Particular preferred is a post-treatment of t-butyl hydroperoxide with aliphatic sulfinic acids (i.e. Bruggolite® FF6) as this reduces possible discoloration of the emulsion polymer as such or when dissolved in the end formulation.

The aqueous dispersion obtained from emulsion polymerization (eventually comprising a post treatment step) can either be incorporated directly into the shampoo preparation according to the present invention, or drying of the dispersion takes place, e.g. spray-drying or freeze-drying, so that the acrylic emulsion polymer can be used and processed in the form of powder.

The acrylic emulsion polymers according to the present invention preferably have a molecular weight between 30-500 kDalton, more preferably 50-250 kDalton and most preferred between 75 and 200 kDalton such as in the range of 100 to 150 kDalton, and a glass transition temperature (Tg) between 40 and 140° C., more preferably between 55 and 130° C. and most preferred between 70-120° C. such as e.g. between 70 and 100° C. Advantageously the emulsion polymers according to the invention have a molecular weight between 75-200 kDalton and a Tg in the range of 70-120° C. such as in particular a molecular weight between 100-150 kDalton and a Tg in the range of 70-100° C.

Preferably, the acrylic emulsion polymer is used in the form of an aqueous dispersion, wherein the dispersion has a polymer solid content in the range of 30 to 60 wt.-%, such as in particular in the range of 35 to 45 wt.-%. In a preferred embodiment this dispersion further contains methylisothiazolinone, in particular in an amount of about 30 to 50 ppm. In a very particular embodiment the aqueous dispersion of the acrylic emulsion polymer according to the invention has a polymer solid content in the range of 35 to 45 wt.-% such as 40 wt.-% and a methylisothiazolinone content of about 50 ppm.

A particular suitable acrylic emulsion polymer according to the present invention is available at DSM Nutritional Products Ltd. under the Tradename TILAMAR® Fix A140 (INCI: acrylates copolymer, Chemical Name: polymer with 2-methyl-2-propenoic acid, butyl 2-methyl-2-propenoate, and ethyl 2-propenoate, CAS Number: 26715-43-5).

The acrylic emulsion polymers to be used in the shampoo preparation according to the present invention are usually partially or completely neutralized, expediently to 5 to 100%, or often to 30 to 95%, using an alkali metal hydroxide or preferably using an amine. In a preferred embodiment, the polymers are partially neutralized, and in a particularly preferred embodiment completely neutralized.

Good neutralization results are often obtained with 2-amino-2-methyl-1-propanol, triiso-propanolamine, triethanolamine, tromethamine, 2-amino-2-ethylpropane-1,3-diol or 3-diethylamino-1-propylamine such as particularly with 2-amino-2-methyl-1-propanol which is e.g. available as AMP-Ultra™ PC 2000 at DOW.

The neutralizing agents are preferably added in the form of a dilute aqueous solution to the acrylic polymer emulsion.

In a particularly preferred embodiment the acrylic emulsion polymers according to the invention are neutralized to at least 50% as then the foam formation of the shampoo is significantly increased compared to a lower neutralization level. Most preferably, the acrylic emulsion polymer is completely neutralized (100%), in particular with 2-amino-2-methyl-1-propanol.

The shampoo preparations according to the invention preferably comprise from 50 to 98 wt.-%, preferably from 50 to 80 wt.-%, of water, based on the total weight of the shampoo preparation.

The shampoo preparations according to the present invention preferably include co-surfactants, to help impart aesthetic, physical or cleansing properties to the compositions. Examples of co-surfactants are nonionic surfactants, which can be included in an amount ranging from 0.5 to 8 wt.-%, preferably from 2 to 5 wt.-% based on the total weight of the shampoo preparation. For example, representative nonionic surfactants that can be included into shampoo preparations according to the invention include condensation products of aliphatic ($C_8$-$C_{18}$) primary or secondary linear or branched chain alcohols with alkylene oxides, usually ethylene oxide and generally having from 6 to 30 ethylene oxide groups. Other representative nonionic surfactants include mono- or di-alkyl alkanolamides such as e.g. coco mono- or di-ethanolamide and coco mono-isopropanolamide. Further nonionic surfactants which can be included in shampoo preparations of the invention are the alkyl polyglycosides (APGs). Typically, the APG is one which comprises an alkyl group connected (optionally via a bridging group) to a block of one or more glycosyl groups such as e.g. Oramix™ NS 10 ex Seppic; PLANTACARE® 818UP, PLANTACARE® 1200 and PLANTACARE® 2000 ex Cognis.

Another example of a co-surfactant is an amphoteric or zwitterionic surfactant, which can be included in an amount ranging from 0.5 to about 8 wt.-%, preferably from 1 to 5 wt.-% based on the total weight of the shampoo preparation. Examples of amphoteric or zwitterionic surfactants include alkyl amine oxides, alkyl betaines, alkyl amidopropyl betaines, alkyl sulphobetaines (sultaines), alkyl glycinates, alkyl carboxyglycinates, alkyl amphoacetates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoo preparations according to the invention include lauryl amine oxide, cocodimethyl sulphopropyl betaine, lauryl betaine, cocamidopropyl betaine (CAPB), sodium cocoamphoacetate and disodium cocoamphodiacetate. Particularly preferred amphoteric or zwitterionic surfactants to be used in the shampoo preparations of the present invention are cocamidopropyl betaine, cocoamphoacetate or cocoamphodiacetate such as most preferably sodium cocoamphoacetate.

Mixtures of any of the foregoing amphoteric or zwitterionic surfactants may also be suitable. Preferred mixtures are those of cocamidopropyl betaine with further amphoteric or zwitterionic surfactants as described above such as in particular with sodium cocoamphoacetate or disodium cocoamphodiacetate.

It has surprisingly been found, that shampoo preparations comprising an additional amount of an amphoteric or zwitterionic surfactant are in particular suitable for improving the styling performance and improving the hair feel. Thus, in an advantageous aspect the shampoo preparations comprise an anionic surfactant and an amphoteric or zwitterionic surfactant. Preferably, the anionic surfactant is selected from ammonium lauryl sulfate, sodium lauryl sulfate, ammonium laureth sulfate and/or sodium laureth sulfate and the amphoteric or zwitterionic surfactant is selected from cocamidopropyl betaine, cocoamphoacetate and/or cocoamphodiacetate. Most preferably the shampoo preparations according to the present invention comprise an anionic surfactant and an amphoteric surfactant anionic surfactant such as in particular sodium laureth sulfate and sodium cocoamphoacetate.

The weight-ratio of the anionic surfactant(s) to the amphoteric and/or zwitterionic surfactants is preferably selected in the range of 5:1 to 1:1, more preferably in the range of 3:1 to 1:1

In another advantageous embodiment the shampoo preparation contains anionic and amphoteric and/or zwitterionic surfactants, preferably only sodium lauryl ether sulfate and sodium cocoamphoacetate, and the weight-ratio of the total amount of the anionic and amphoteric and/or zwitterionic surfactants to the acrylic emulsion polymer is selected in the range of 5:1 to 1:1, preferably in the range of 3:1 to 1:1, most preferably in the range of about 2.5:1 to 2:1.

The shampoo preparations according to the invention can contain further ingredients to enhance the performance and/or consumer acceptability such as preservatives, antioxidants, fatty substances/oils, thickeners, softeners, emulsifiers, light-screening agents, antifoaming agents, moisturizers, fragrances, co-surfactants, fillers, sequestering agents, cationic-, nonionic- or amphoteric polymers or mixtures thereof, acidifying or basifying agents, dyes, colorants, pigments or nanopigments, pearlizers or opacifiers, organic or inorganic particles, viscosity modifiers, and natural hair nutrients such as botanicals, fruit extracts, sugar derivatives and/or amino acids or any other ingredients usually formulated into rinse off compositions. The necessary amounts of the adjuvants and additives can, based on the desired product, easily be chosen by a person skilled in the art in this field and will be illustrated in the examples, without being limited hereto.

The shampoo preparations according to the invention may also comprise a hydrotrope. A hydrotrope is a substance that improves the solubility of surfactants in water. Examples of hydrotropes are sodium xylene sulfonate, ammonium xylene sulphonate, sodium p-toluene sulfonate, sodium chlorobenzene sulfonate, sodium salicylate, proline, pyrogallol, resorcinol and urea. In all embodiments of the invention preferably sodium xylene sulfonate is used as hydrotrope. The total amount of the hydrotrope in the compositions according to the invention ranges typically from 0.5 to 30 wt.-%, preferably from 1 to 20 wt.-%, in particular from 1 to 5 wt.-% based on the total weight of the preparation.

The shampoo preparation of the invention may further comprise a suspending agent. Suitable suspending agents are selected from polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and polyethylene glycol 3 distearate are preferred long chain acyl derivatives, since these impart pearlescence to the composition. Polyacrylic acid is available commercially as Carbopol® 420, Carbopol® 488 or Carbopol® 493. Polymers of acrylic acid cross-linked with a polyfunctional agent may also be used; they are available commercially as Carbopol® 910, Carbopol® 934, Carbopol® 941, Carbopol® 980 and Carbopol® Ultrez 10 Polymer. Examples of suitable copolymers of a carboxylic acid containing monomer and acrylic acid esters are Carbopol® 1342, Carbopol® Ultrez 20 or Carbopol® Ultrez 21, Pemulen TR1 or Pemulen TR2. All Carbopol® or Pemulen® materials are available from Noveon Consumer Specialities.

A suitable heteropolysaccharide gum is xanthan gum, for example Keltrol®-types or Kelzan®-types from Kelco, Vanzan NF from RT Vanderbilt Inc. or Rhodicare®-types from Rhodia.

Mixtures of any of the above suspending agents may be used. Preferred is a mixture of cross-linked polymer of acrylic acid and crystalline long chain acyl derivative.

The suspending agent(s) will generally be used at levels of from 0.1 to 10 wt.-%, preferably from 0.5 to 6 wt.-%, more preferably from 0.9 to 4 wt.-%, based on the total weight of the shampoo preparation.

The shampoo preparations according to the invention may further contain anti dandruff agents. Examples of anti-dandruff agents which may be used are cimbazole, octopirox and zinc pyrithione. Customary film formers include, for example, chitosan, microcrystalline chitosan, quaternized chitosan, polyvinylpyrrolidone, vinylpyrrolidone/vinyl acetate copolymers, polymers of quaternary cellulose derivatives containing a high proportion of acrylic acid, collagen, hyaluronic acid and salts thereof and similar compounds.

The shampoo preparations according to the invention may further contain UV-filter substances. Examples of UV-filter substances suitable for the incorporation into the compositions according to the invention include benzophenones such as e.g. benzophenones-4 or benzophenones-3, acrylates such as 2-ethylhexyl 2-cyano-3,3-diphenylacrylate (octocrylene, PARSOL® 340), cinnamate derivatives such as ethylhexyl methoxycinnamate (PARSOL® MCX), benzalmalonate derivatives bond to siloxanes such as e.g. polysilicones-15 (PARSOL® SLX), salicylate derivatives such as isopropylbenzyl salicylate, benzyl salicylate, butyl salicylate, ethylhexyl salicylate (PARSOL® EHS, Neo Heliopan OS), isooctyl salicylate or homomenthyl salicylate (homosalate, PARSOL® HMS, Neo Heliopan HMS), benzotriazole derivatives such as sodium benzotriazolyl butylphenol sulfonate, imidazole derivatives such as e.g. 2-phenyl benzimidazole sulfonic acid and its salts (PARSOL® HS), dibenzoylmethane derivatives such as (avobenzone, Parsol® 1789) without being limited thereto.

The viscosity of the hair styling shampoo preparations according to the invention is preferably selected in the range of 500 and about 20000 mPa·s at 20° C., preferably 1000 to 10000, in particular 1000 to 7000 mPa·s at 20° C., measured with Brookfield or Höppler viscosimeters at a shear rate of 10 sec-1. The viscosity of the shampoo compositions can be adjusted with known viscosity enhancers (thickeners). Preferred viscosity enhancers are PEG-55 propyleneglycol oleate and PEG-18 glyceryl oleate/cocoate known with the trade names Antil® 141 and 171, respectively and PEG-160 sorbitan triisostearate known with a trade name RHEODOL TW-IS399C such as most preferably PEG-18 glyceryl oleate/cocoate. It should be noted that in the case that a preparation is delivered in the form of a foam from a pump-foamer and/or aerosol can, those compositions should not be thickened and have a viscosity value not more than 500 mPa·s, more preferably 250 mPa·s measured as mentioned above at 20° C.

In a particular advantageous embodiment according to the present invention the shampoo preparation consists of
(a) 50 to 80 wt.-% of water,
(b) 1 to 10 wt.-% of an acrylic emulsion polymer obtained by emulsion polymerization of a monomer composition consisting of a mixture of 10-30 wt.-% of methacrylic acid, 5-15 wt.-% of ethyl acrylate and 60-80 wt.-% of n-butyl methacrylate,
(c) 2 to 15 wt.-% of an anionic surfactant,
(d) 1 to 5 wt.-% of a amphoteric or zwitterionic co-surfactant and
(e) 1 to 10 wt.-% of additional agents
with the proviso that all ingredients sum up to 100 wt.-%. Preferably, the anionic surfactant is sodium lauryl ether sulfate and the amphoteric or zwitterionic co-surfactant is sodium cocoamphoacetate and the acrylic emulsion polymer is one obtained by emulsion polymerisation of a monomer mixture consisting of 15-25 wt.-% of methacrylic acid, 8-12 wt.-% of ethyl acrylate and 65-75 wt.-% of n-butyl methacrylate, more preferably of 18-23 wt.-% of methacrylic acid, 9-11 wt.-% of ethyl acrylate and 67-72 wt.-% of n-butyl methacrylate. With regard to the additional agents reference is made to the handbooks known to the person skilled in the art, e.g. K. Schrader, Grundlagen and Rezepturen der Kosmetika [Bases and Formulations in Cosmetics], 2nd edition, Huthig Buch Verlag, Heidelberg, 1989. Exemplary additional agents include thickening agents, perfume, sodium chloride, sodium benzoate without being limited thereto.

In a further embodiment, the invention is concerned with a method of treating, such as preferably styling, the hair comprising the step of applying a shampoo preparation according to the invention to the hair. In a particular embodiment, the method involves the steps of shampooing the hair, rinsing the hair with water and optionally drying the hair and appreciating the styling effect and the hair feel.

The amount of the hair styling shampoo preparation used for shampooing the hair is preferably selected in the range of about 1 g to about 20 g (per application on a human head).

The invention is further illustrated with reference to the following, non-limiting examples, in which all percentages are by weight based on total weight unless otherwise specified.

EXAMPLE 1

Foaming

The shampoo preparations outlined in table 1 have been prepared by dissolving AMP-Ultra™ PC 2000 (when present) in water. Afterwards TILAMAR® Fix A140 was added and the resulting mixture was stirred until complete dissolution. Afterwards the residual ingredients were added consecutively under dissolution. The foaming performance was assessed on mannequin heads. Thus, the hair was wetted and the hair was shampooed with 5 g of the respective shampoo and the foaming was assessed visually. The results are illustrated in table 1.

TABLE 1

| Tradename | INCI | 1 | 2 | 3 |
|---|---|---|---|---|
| | | | Wt.-% | |
| Water | Aqua | | Ad 100 | |
| TILAMAR ® Fix A140 (40% solution) | Acrylates copolymer | 12.5 | 12.5 | 12.5 |
| AMP-Ultra ™ PC 2000 (95% solution) | Aminomethyl Propanol | — | 0.62 | 1.24 |
| Texapon ® NSO-BZ (28% solution) | Sodium laureth sulfate | 27 | 27 | 27 |
| Miranol ® Ultra C32 (40% solution) | Sodium Cocoamphoacetate | 8 | 8 | 8 |
| Purox S | Sodium benzoate | 0.5 | 0.5 | 0.5 |
| Sodium chloride | Sodium chloride | 2 | 2 | 2 |
| Pö Color Express 351580 | Perfume | 0.5 | 0.5 | 0.5 |
| Citric Acid | Citric acid | 0.5 | 0.5 | 0.5 |
| Neutralisation Level | | 0% | 50% | 100% |
| Foaming | | little | good | good |

As can be retrieved from table 1, good foaming was achieved at a neutralization level of 50% or more.

EXAMPLE 2

Sensory Test

The shampoo preparations according to table 2 have been prepared by dissolving AMP-Ultra™ PC 2000 in water. Afterwards TILAMAR® Fix A140 has been added and the resulting mixture has been stirred until complete dissolution (100% neutralization level). Afterwards the residual ingredients have been added consecutively under dissolution.

Then the shampoos were tested on hair tresses (12 cm, European hair, 10 cm free hair). The hair tresses were wetted with water; afterwards the tresses were treated with 0.5 ml of the respective shampoo and shampooed for 30 sec. Then the hair tresses were rinsed with tab water (T=38° C., ca. 5 l/min) for 1 min and afterwards combed 5 times. After the hair tresses have been dried at 40° C. for 1 h in a drying oven the hair tresses were evaluated for their styling attributed (hold and body) and feel. The results of the sensory evaluation are summarized in table 3.

TABLE 2

| Tradename | INCI | 1 | 2 | 3 | 4 | Ref. |
|---|---|---|---|---|---|---|
| | | | | Wt.-% | | |
| Water | Aqua | | | Ad 100 | | |
| TILAMAR ® Fix A140 (40% solution) | Acrylates copolymer | 12.5 | 10 | 8 | 6 | — |
| PVP K-30 (30% solution) | Polyvinyl-pyrrolidon | — | — | — | — | 10 |
| AMP-Ultra ™ PC 2000 (95% solution) | Aminomethyl Propanol | 1.25 | 1 | 0.8 | 0.6 | 0.6 |
| Texapon ® NSO-BZ (28% solution) | Sodium laureth sulfate | 13.5 | 13.5 | 13.5 | 13.5 | 13.5 |
| Miranol ® Ultra C32 (40% solution) | Sodium Coco-ampho-acetate | 4 | 4 | 4 | 4 | 4 |
| Purox ® S | Sodium benzoate | 0.5 | 0.5 | 0.5 | 0.5 | 0.5 |
| Sodium chloride | Sodium chloride | 2 | 2 | 2 | 2 | 2 |
| Pö Color Express 351580 | Perfume | 0.5 | 0.5 | 0.5 | 0.5 | 0.5 |

TABLE 2-continued

| Tradename | INCI | 1 | 2 | 3 Wt.-% | 4 | Ref. |
|---|---|---|---|---|---|---|
| Citric Acid | Citric acid | 0.5 | 0.5 | 0.5 | 0.5 | 0.5 |
| Antil ® 171 | PEG-18 Glyceryl Oleate/Cocoate | 2 | 2 | 2 | 2 | 2 |

TABLE 3

Sensory evaluation

| Nr. | Foam | Wet feel | Dry feel | Styling performance |
|---|---|---|---|---|
| 1 | Good | Soft | Soft | Good |
| 2 | Good | Soft | Soft | Good |
| 3 | Good | Soft | Soft | Good |
| 4 | Good | Soft | Soft | Good |
| Ref. | Good | Dull, brittle | Dull, brittle | Good |

As can be retrieved from the results in table 3, the shampoo preparations according to the present invention yield a good styling performance while providing a soft feel to the hair.

EXAMPLE 3

The sensory properties of the shampoo preparation No. 1 of table 2 were also assessed on a mannequin head. First the hair was washed 5 g with a standard shampoo (Water 57.5%, Texapon® NSO-BZ 35%, Tego Betain F50 5%, Purox S 0.5%, Citric Acid 0.5%, NaCl 1.5%), rinsed with tab water and dried with a hair dryer at medium heat. Afterwards, half of the mannequin head was treated with 5 g the shampoo preparation, rinsed with tab water and dried with a hair dryer at medium heat. The other half of the mannequin hair was not treated. The comparative assessment revealed that the hair treated with the shampoo according to the present exhibited better hold and body while having a soft and smooth touch.

EXAMPLE 4

Exemplary Shampoo Preparation (All amounts given are based on the active ingredients).

| INCI Nomenclature | wt. % (as active) |
|---|---|
| 4.1 Styling shampoo | |
| Sodium Laureth Sulfate | 10.00 |
| Ammonium Lauryl Sulfate | 5.00 |
| Water | 40.00 |
| Cocamidopropyl Betaine | 2.50 |
| *Borago Officinalis* Seed Oil & Tocopherol & Ascorbyl Palmitate | 0.30 |
| PEG-40 Hydrogenated Castor Oil | 0.50 |
| Fragrance | 0.30 |
| Panthenol | 1.00 |
| Disodium EDTA | 0.10 |
| Water | 10.00 |
| Sodium benzoate | 0.50 |
| Citric acid | 0.2 |
| Acrylates copolymer (TILAMAR ® Fix A140) | 2.4 |
| Aminomethyl Propanol | 0.6 |
| Sodium Chloride | 2.00 |
| PEG-150 Pentaerythrityl Tetrastearate | 3.00 |
| Water | ad. 100 |
| 4.2 Hydrating Shampoo with styling effect | |
| Sodium Myreth Sulfate | 10.00 |
| Ethylhexyl Methoxycinnamate | 0.30 |
| Sodium Benzoate | 0.50 |
| Citric Acid | 0.20 |
| Panthenol | 1.00 |
| PEG-7 Glyceryl Cocoate | 2.00 |
| Cocamidopropyl Betaine | 3.50 |
| Glycol Distearate & Glycerin and Laureth-4 & Cocamidopropyl Betaine | 2.00 |
| Disodium EDTA | 0.10 |
| Perfume | 0.80 |
| Polyquaternium-10 | 0.10 |
| Decyl Glucoside | 10.00 |
| Sodium Chloride | 1.50 |
| Acrylates copolymer (TILAMAR ® Fix A140) | 5.00 |
| Aminomethyl Propanol | 1.23 |
| PEG-18 Glyceryl Oleate/Cocoate | 1.00 |
| Aqua (water) | Ad 100 |
| 4.3 Hydrating Shampoo for Color Protection with volumizing effect | |
| Sodium Laureth Sulfate | 15.00 |
| Polysilicone-15 | 0.30 |
| Methylchloroisothiazolinone & Methylisothiazolinone | 0.10 |
| Panthenol | 1.00 |
| PEG-7 Glyceryl Cocoate | 2.00 |
| Cocamidopropyl Betaine | 3.50 |
| Glycol Distearate & Glycerin and Laureth-4 & Cocamidopropyl Betaine | 2.00 |
| Disodium EDTA | 0.10 |
| Fragrance | 0.80 |
| Polyquaternium-10 | 0.10 |
| Decyl Glucoside | 10.00 |
| Aqua (water) | Ad 100 |
| Acrylates copolymer (TILAMAR ® Fix A140) | 4 |
| Aminomethyl Propanol | 1.08 |
| Sodium Chloride | 1.50 |
| PEG-18 Glyceryl Oleate/Cocoate | 1.00 |
| 4.4 Anti Dandruff Shampoo with styling effect | |
| Aqua (water) | Ad 100 |
| Ammonium laureth sulfate | 10.00 |
| Ammonium lauryl sulfate | 5.00 |
| Glycol distearate | 1.00 |
| Dimethicone | 1.00 |
| Cetyl alcohol | 0.50 |
| Cocamide MEA | 3.00 |
| ZPT | 1.00 |
| Guar hydroxypropyltrimonium chloride | 0.20 |
| Hydrogenated polydecene | 1.00 |
| Polyquaternium 10 | 0.30 |
| PEG 7m | 0.50 |
| Trimethylpropane tricaprylate/tricaprate | 1.00 |
| Preservative | q.s. |
| Fragrance | 0.30 |
| E 104, E 110, E 132 | 0.02 |
| Acrylates copolymer (TILAMAR ® Fix A140) | 6.40 |
| Aminomethyl Propanol | 1.58 |
| 4.5 Styling shampoo with plant extracts | |
| Aqua (water) | Ad 100 |
| Sodium laureth sulfate | 10.00 |
| Lauryl glucoside | 6.00 |
| Cocamidopropyl betaine | 2.00 |
| Propylene glycol | 2.00 |
| Perfume oil | 1.25 |
| Sodium citrate | 0.25 |
| Sodium benzoate | 0.20 |
| Panthenol | 1.00 |
| Sodium formate | 0.20 |
| Polyquaternium-10 | 0.20 |

-continued

| INCI Nomenclature | wt. % (as active) |
|---|---|
| Hydroxypropyl guar hydroxypropyltrimonium chloride | 0.05 |
| PEG-35 castor oil | 1.00 |
| Maris sal | 1.25 |
| Polysorbate 20 | 1.00 |
| Tocopheryl acetate | 0.20 |
| *Prunus armeniaca* | 0.20 |
| *Echinacea purpurea* | 0.05 |
| Retinyl palmitate | 0.05 |
| Tocopherol | 0.05 |
| Linoleic acid | 0.20 |
| Preservative | 1.00 |
| Acrylates copolymer (TILAMAR ® Fix A140) | 5.00 |
| Aminomethyl Propanol | 1.23 |
| CI77891 | 0.02 |

The invention claimed is:

1. A shampoo preparation comprising:
   water,
   at least one anionic surfactant selected from the group consisting of sodium lauryl sulfate, ammonium lauryl sulfate, sodium lauryl ether sulfate and ammonium lauryl ether sulfate;
   an amphoteric and/or zwitterionic co-surfactant selected from the group consisting of cocamidopropyl betaine, cocoamphoacetate and cocoamphodiacetate, and
   an effective amount of an acrylic emulsion polymer which is an emulsion polymerization product of a monomer mixture consisting of 10-30 wt.-% of methacrylic acid, 5-15 wt.-% ethyl acrylate and 60-80 wt.-% of n-butyl methacrylate, wherein
   the anionic surfactant and the amphoteric and/or zwitterionic co-surfactant are present in an amount to provide a ratio of the anionic surfactant to the amphoteric and/or zwitterionic co-surfactant of 5:1 to 1:1.

2. The shampoo preparation according to claim 1, wherein the acrylic emulsion polymer is present in an effective amount of 0.01-20 wt.-%, based on the total weight of the shampoo preparation.

3. The shampoo preparation according to claim 1, wherein the anionic surfactant is present in an amount of 0.1 to 25 wt.-%, based on the total weight of the shampoo preparation.

4. The shampoo preparation according to claim 1, wherein the water is present in an amount of 50 to 80 wt.-%, based on the total weight of the shampoo preparation.

5. The shampoo preparation according to claim 1, wherein the acrylic emulsion polymer is an aqueous dispersion having a polymer solid content in a range of 30 to 60 wt.-%.

6. The shampoo preparation according to claim 1, wherein the acrylic emulsion polymer is neutralized to a degree of at least 50%.

7. A method of treating hair comprising applying an effective amount of the shampoo preparation according to claim 1 to hair in need of treatment.

8. A method according to claim 7, which method comprises shampooing the hair with about 1 to 20 g of the shampoo preparation and then rinsing the hair with water.

9. The method according to claim 8, further comprising the step of drying the hair and appreciating the styling effect and the hair feel.

* * * * *